(12) United States Patent
Cheetham et al.

(10) Patent No.: US 6,552,087 B1
(45) Date of Patent: Apr. 22, 2003

(54) THERAPEUTIC AGENT COMPRISING (+)-SIBUTRAMINE

(75) Inventors: Sharon C. Cheetham, Nottinghamshire (GB); David John Heal, Nottinghamshire (GB)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/527,659

(22) Filed: Mar. 17, 2000

Related U.S. Application Data

(60) Provisional application No. 60/125,320, filed on Mar. 19, 1999.

(51) Int. Cl.⁷ ............................................. A61K 31/36
(52) U.S. Cl. .................... 514/646; 514/909; 514/910; 514/878; 514/879
(58) Field of Search .............................. 514/646, 909, 514/910, 878, 879

(56) References Cited

U.S. PATENT DOCUMENTS

| | | | | |
|---|---|---|---|---|
| 4,522,828 A | * | 6/1985 | Jeffery et al. ................ | 514/646 |
| 4,939,175 A | | 7/1990 | Ukai et al. ................... | 514/646 |
| 5,436,272 A | * | 7/1995 | Scheinbaum ................. | 514/646 |
| 6,323,242 B1 | | 11/2001 | Mueller ....................... | 514/646 |

FOREIGN PATENT DOCUMENTS

| | | |
|---|---|---|
| EP | 230742 | 9/1990 |
| EP | 282206 | 11/1990 |
| EP | 397831 | 9/1993 |
| GB | 2098602 A | 11/1982 |
| WO | WO 95/20949 | 8/1995 |
| WO | WO 98/11884 | 3/1998 |
| WO | WO 98/13033 | 4/1998 |
| WO | WO 98/13034 | 4/1998 |

* cited by examiner

*Primary Examiner*—Frederick Krass
(74) *Attorney, Agent, or Firm*—Tara Seshadri

(57) ABSTRACT

The use of (+)-sibutramine in the treatment of depression, obesity, Parkinson's disease, cerebral function disorders and diabetes is described.

29 Claims, No Drawings

US 6,552,087 B1

THERAPEUTIC AGENT COMPRISING (+)-SIBUTRAMINE

RELATED APPLICATIONS

This application claims priority to U.S. Provisional Application Serial No. 60/125,320, entitled "Therapeutic Agent," filed on Mar. 19, 1999; the entire contents of which are hereby incorporated herein by reference.

BACKGROUND OF THE INVENTION

The preparation and use of compounds, such as N,N,-dimethyl-1-[1-(4-chlorophenyl)cyclobutyl]-3-methylbutylamine (or N-{1-[1-(4-chlorophenyl)cyclobutyl]-3-methylbutyl}-N,N-dimethylamine) and salts thereof, in the treatment of depression is described in British Patent Specification 2098602. The use of compounds such as N,N,-dimethyl-1-[1-(4-chlorophenyl)cyclobutyl]-3-methylbutylamine and salts thereof in the treatment of Parkinson's disease is described in European Patent Number 282206. The use of compounds such as N,N,-dimethyl-1-[1-(4-chlorophenyl)cyclobutyl]-3-methylbutylamine and salts thereof in the treatment of cerebral function disorders is described in U.S. Pat. No. 4,939,175. The use of N,N,-dimethyl-1-[1-(4-chlorophenyl)cyclobutyl]-3-methylbutylamine hydrochloride in the treatment of obesity is described in European Patent Number 397831. A particularly preferred form of this compound is N,N,-dimethyl-1-[1-(4-chlorophenyl)cyclobutyl]-3-methylbutylamine hydrochloride monohydrate (sibutramine hydrochloride monohydrate) which is described in European Patent Number 230742. The use of N,N,-dimethyl-1-[1-(4-chlorophenyl)cyclobutyl]-3-methylbutylamine and salts thereof for improving the glucose tolerance of humans having Impaired Glucose Tolerance or Non-Insulin Dependent Diabetes Mellitus is described in published PCT application WO95/20949.

All of the above documents are incorporated herein by reference.

The use of sibutramine as an insulin sensitiser is disclosed in WO98/11884. The use of sibutramine in lowering uric acid levels is disclosed in WO98/13033. The use of sibutramine in lowering lipid levels is disclosed in WO98,13034.

SUMMARY OF THE INVENTION

This invention relates to the (+)-enantiomer of Sibutramine, which is N,N-dimethyl-1-[1-(4-chlorophenyl)cyclobutyl]-3-methylbutylamine, and pharmaceutically acceptable salts thereof, to their use in the treatment of obesity and depression, to formulations containing these compounds and to methods for their preparation.

DETAILED DESCRIPTION OF THE INVENTION

The present invention provides a method of treating any of the indications previously disclosed as being treatable by racemic sibutramine in any of the above documents comprising administering to a mammal, particularly a human, in need thereof a therapeutically effective amount of (+)-sibutramine or a pharmaceutically acceptable salt thereof, substantially free of its (−)-enantiomer.

In particular (+)-sibutramine is useful in the treatment of depression, obesity, Parkinson's disease, cerebral function disorders and diabetes.

The present invention provides a method of treating depression in a human which comprises administering to a human in need of antidepressant therapy, an amount of (+)-sibutramine, or a pharmaceutically acceptable salt thereof, substantially free of its (−)-stereoisomer, said amount being sufficient to alleviate depression.

In another aspect the present invention provides a method for treating obesity or weight gain in a human which comprises administering to a human in need of a reduction in weight, an amount of (+)-sibutramine or a pharmaceutically acceptable salt thereof, substantially free of its (−)-stereoisomer, said amount being sufficient to alleviate obesity or weight gain.

In yet another aspect the present invention provides a method of treating disorders ameliorated by inhibition of neuronal monoamine reuptake in a human which comprises administering to a human in need of such treatment an amount of (+)-sibutramine or a pharmaceutically acceptable salt thereof, substantially free of its (−)-stereoisomer, said amount being sufficient to alleviate said disorders. Preferably said monoamine is dopamine. Preferably said disorder is Parkinson's disease.

In yet another aspect the present invention provides a method for treating cerebral function disorders in humans which comprises administering to a human an amount of (+)-sibutramine, or a pharmaceutically acceptable salt thereof, substantially free of its (−)-stereoisomer, said amount being sufficient to alleviate cerebral function disorders. In a preferred embodiment the cerebral function disorder is caused by a cerebrovascular disease. In another preferred embodiment the cerebral function disorder is selected from the group consisting of senile dementia, Alzheimer's type dementia, memory loss and amnesia/amnestic syndrome. Preferably the cerebrovascular disease is selected from the group consisting of cerebral infarction, cerebral bleeding, cerebral arteriosclerosis, cerebral venous thrombosis and head injuries.

The above inventions provide in preferred embodiments methods of treating depression, obesity, weight gain, disorders ameliorated by inhibition of neuronal monoamine reuptake or cerebral function disorders in a human in which said amount of (+)-sibutramine or a pharmaceutically acceptable salt thereof, substantially free of its (−)-stereoisomer, is sufficient to alleviate the said disease or disorder but insufficient to cause adverse effects associated with the administration of racemic sibutramine.

Examples of pharmaceutically acceptable salts of (+)-sibutramine include the hydrochloride, hydrobromide, sulphate, methanesulphonate, nitrate, maleate, acetate, citrate, fumarate, tartrate [e.g. (+)-tartrate, (−)-tartrate or mixtures thereof including racemic mixtures], succinate, benzoate, benzenesulphonate, camphorsulphonate, gluconate, lactate, malate, mandelate, pamoate, phosphate, p-toluenesulphonate and salts with amino acids such as glutamic acid. Preferably the salt is the hydrochloride salt.

In another aspect the present invention provides a composition for the treatment of depression in a human which comprises an amount of (+)-sibutramine or a pharmaceutically acceptable salt thereof, substantially free of its (−)-stereoisomer, said amount being sufficient to alleviate depression.

In a further aspect the present invention provides a composition for the treatment of depression in a human wherein said amount of (+)-sibutramine, or a pharmaceutically acceptable salt thereof, is sufficient to treat depression but insufficient to cause adverse effects associated with the administration of racemic sibutramine.

In another aspect the present invention provides a composition for treating obesity or weight gain in a human which comprises an amount of (+)-sibutramine or a pharmaceutically acceptable salt thereof, substantially free of its (−)-stereoisomer, said amount being sufficient to alleviate obesity or weight gain.

In a further aspect the present invention provides a composition for treating weight disorders in a human wherein said amount is sufficient to alleviate obesity or weight gain in a human but insufficient to cause adverse effects associated with administration of racemic sibutramine.

In another aspect the present invention provides a composition for the treatment of disorders ameliorated by inhibition of neuronal monoamine reuptake in a human which comprises an amount of (+)-sibutramine or a pharmaceutically acceptable salt thereof, substantially free of its (−)-stereoisomer, said amount being sufficient to alleviate said disorders.

In a further aspect the present invention provides a composition for the treatment of disorders ameliorated by inhibition of neuronal monoamine reuptake in a human wherein said amount of (+)-sibutramine or a pharmaceutically acceptable salt thereof, is sufficient to treat said disorders but insufficient to cause adverse effects associated with the administration of racemic sibutramine.

In another aspect the present invention provides a composition for treating cerebral function disorders, which comprises an amount of (+)-sibutramine or a pharmaceutically acceptable salt thereof, substantially free of its (−)-stereoisomer, said amount being sufficient to alleviate cerebral function disorders.

In a further aspect the present invention provides a composition for treating cerebral function disorders wherein said amount of (+)-sibutramine or a pharmaceutically salt thereof, substantially free of its (−)-stereoisomer, is sufficient to treat cerebral function disorders but insufficient to cause the adverse effects associated with the administration of racemic sibutramine.

Preferably the above compositions comprise (+)-sibutramine and a pharmaceutically acceptable diluent or carrier. In the following the term active compound means (+)-sibutramine or a pharmaceutically acceptable salt thereof.

The active compound may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range from 0.1 to 100 mg, preferably 1 to about 60 mg per day, more preferably from about 2 mg to about 50 mg per day and most preferably from about 5 mg to about 45 mg per day. Especially preferred dosages are 5 mg, 10 mg, 15 mg and 20 mg per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropyl-methylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently. each contain 0.1 to 100 mg, preferably 1 to about 60 mg per day, more preferably from about 2 mg to about 50 mg per day and most preferably from about 5 mg to about 45 mg per day. Especially preferred dosages are 5 mg, 10 mg, 15 mg and 20 mg per day given in one or more doses.

Other dosage forms for oral administration include, for example, aqueous suspensions containing the active compound in an aqueous medium in the presence of a non-toxic suspending agent such as sodium carboxy-methylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, e.g. an effervescent couple formed from an acid and a carbonate or bicarbonate salt to facilitate dispersion in the liquid medium.

The active compound may be formulated into a composition which the patient retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The active compound may be formulated into a composition which is dispersed as an aerosol into the patients oral or nasal cavity. Such aerosols may be administered from a pump pack or from a pressurised pack containing a volatile propellant.

The active compound used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a very sparingly water-soluble derivative such as a dodecanoate salt or a lipophilic ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The term "adverse effects" as used herein includes, but is not limited to increases in heart rate, increases in blood pressure including systolic blood pressure, increased psychomotor activity, dry mouth, tension and nervousness.

The term "substantially free of its (−)-stereoisomer", as used herein, means that the composition contains a greater proportion of the (+)-stereoisomer of sibutramine in relation to the (−)-isomer of sibutramine. The term "substantially free of its (−)-stereoisomer" includes a composition containing an amount of the (+)-stereoisomer of sibutramine in relation to the (−)-isomer of sibutramine such that the composition can perform its intended function, e.g., of treating the selected indication, e.g., treating obesity, weight gain, and/or depression. In a preferred embodiment of the present invention the term "substantially free of its (−)-stereoisomer" as used herein means that the composition contains at least 90% by weight of (+)-sibutramine and 10% by weight or less of (−)-sibutramine. In the most preferred embodiment, the term "substantially free of its (−)-stereoisomer" means that the composition contains at least 99% by weight of (+)-sibutramine and 1% or less of (−)-sibutramine. In another preferred embodiment, the term "substantially free of its (−)-stereoisomer" as used herein means that the composition contains 100% by weight of the (+)-isomer of sibutramine. The above percentages are based on the total amount of sibutramine present in the composition. The terms "substantially optically pure (+)-sibutramine", "optically pure (+)-sibutramine" and "(+)-isomer of sibutramine" are also encompassed by the above described amounts.

The invention is illustrated by the following Examples which are given by way of example only. The final product of each of these Examples was characterised by one or more of the following procedures: gas-liquid chromatography; high performance liquid chromatography; elemental analysis, nuclear magnetic resonance spectroscopy and infrared spectroscopy.

EXEMPLIFICATION OF THE INVENTION

The (+)-enantiomer of sibutramine was obtained by N,N-dimethylation of the (+)-enantiomer of the primary amine precursor which was obtained by resolution of racemic 1-[1-(4-chlorophenyl)cyclobutyl]-3-methylbutylamine, which was prepared according to GB 2098602. (S)-(+)-N-carbamoylphenylalanine was mixed with the racemic primary amine in methanol to give a diastereoisomeric mixture of salts. One salt crystallised preferentially from the mixture and this was recrystallised from methanol and basified to afford the (+)-primary amine which had an optical purity >98% (by nmr). Concentration of the filtrate gave the other salt which upon similar treatment gave the (−)-primary amine. The two primary amines were N,N-dimethylated by methods described in GB 2098602 to give the tertiary amines which were converted into their hydrochloride salts. Both the (+)-tertiary amine hydrochloride and the (−)-tertiary amine hydrochloride were at least 98% optically pure by NMR. Analytical data for these two samples are given below.

Physicochemical Data for (+)-N-{1-[1-(4-chlorophenyl)cyclobutyl]-3-methylbutyl}-N,N,-diethylamine hydrochloride m.p. 232° C.

$[\alpha]_D=+4.5°$ (c=2.61; ethanol)

Optical purity: >98% by nmr

Elemental analysis: $C_{17}H_{26}ClN \cdot HCl$ requires: C=64.6; H=8.5; N=4.4; Cl=22.5% Found: C=65.0; H=8.6; N=4.5; Cl=22.8%

The absolute stereochemistry was determined X-ray crystallography and found to be R Physicochemical Data for (−)-N-{1-[1-(4-chlorophenyl)cyclobutyl]-3-methylbutyl}-N,N-dimethylamine hydrochloride m.p. 232° C.

$[\alpha]_D=-4.9°$ (c=3.8; ethanol)

Optical purity: >98% by NMR

Elemental analysis: $C_{17}H_{26}ClN \cdot HCl$ requires: C=64.6; H=8.5; N=4.4; Cl=22.5% Found: C=64.2; H=8.6; N=4.5; Cl=22.9%

The absolute stereochemistry was determined X-ray crystallography and found to be S.

In Vitro Tests

Materials

Animal brain tissue was obtained from adult male Sprague-Dawley derived CD rats (150–250 g) Charles River (Margate). Human tissue was obtained at post-mortem at St. George's Hospital (Tooting, London) from subjects who died suddenly from causes not involving the central nervous system and were without documented evidence of mental illness. Compounds were obtained from the following sources: citalopram (Lundbeck, Valby) and mazindol, (Research Biochemicals International, Natick).

Radioisotopes and Reagents

Radioisotopes were obtained from the following suppliers: [propylene-2,3-$^3$H]-GBR 12935 (40–60 Ci/mmol), [N-methyl-$^3$H]-nisoxetine hydrochloride (70–87 Ci/mmol) and [phenyl-6'-$^3$H]-paroxetine (15–30 Ci/mmol), were obtained from New England Nuclear Research Products, UK. All other reagents were of analytical grade purity and were obtained from Fisher (Loughborough), Sigma (Poole) or BDH (Poole).

Methods

Buffer and Compound Preparation

All buffers were prepared using distilled water. Compounds were dissolved at a concentration of $10^{-2}$ or $10^{-3}$ M in distilled water.

Inhibition Constants ($K_i$ Values)

The concentration of compound required to inhibit 50% of specific binding ($IC_{50}$) was calculated using an iterative curve fitting program (Equilibrium Binding Data Analysis: EBDA) into which count data (dpm) were entered directly from the Liquid Scintillation Analyser. This program calculates specific binding in the absence and presence of a range of concentrations of compound and then converts the specific binding values in the presence and absence of each concentration of compound into percentages of specific binding in the absence of compound as described below.

Specific binding in the absence of compound:

A(dpm)=Total binding (dpm)−Non-specific binding(dpm).

Specific binding in the presence of compound (e.g. $10^{-10}$M):

B(dpm)=Binding $10^{-10}$M(dpm)−Non-specific binding(dpm).

Percentage specific binding in the presence of compound (e.g. $10^{-10}$M):

% Specific binding $10^{-10}$M=B(dpm)/A(dpm)×100.

This is repeated for each concentration of compound tested.

The percentage specific binding at each concentration of compound was then plotted against the logarithm$_{10}$ of the concentration of compound. The IC$_{50}$ was calculated using the following formula:

$$\% \text{ Specific binding} = \frac{(100 - D^p)}{(D^p + IC_{50}^p)}$$

where
100=maximum binding (ie binding in the absence of compound)
P=slope factor which is analogous to the Hill slope
D=concentration of compound (M).

The Hill slope is calculated to detect deviations from simple one-site interactions. A Hill slope approximating to unity indicates displacement from a single site, significantly less than unity indicates displacement from multiple sites and significantly greater than unity indicates positive cooperativity.

The affinity constant ($K_i$) of the compound for the uptake or binding site was then calculated using the Cheng and Prusoff equation:

$$K_i = \frac{IC_{50}}{1 + [L]/K_d}$$

where

[L]=the concentration of radioligand (M)
$K_d$=the affinity of the uptake or binding site for the radioligand.

The concentration of radioligand [L] nM =

$$\frac{\text{dpm } (total\ assay\ radioligand)}{SA \times (2.22 \times 10^{12})} \times \frac{1}{assay\ volume}$$

where SA=specific activity of the radioligand (Ci/mmol).

Binding Assays

The affinities of the (+)- and (−)-enantiomers of sibutramine and racemic sibutramine for monoamine reuptake sites were determined, in vitro, by radioligand binding techniques. The experimental methods employed are summarised in Table 1.

TABLE 1

A summary of the assay methods used to determine the affinity of the (+)- and (−)-enantiomers of sibutramine and racemic sibutramine for monoamine reuptake sites

|  | Rat | | | Human | | |
| --- | --- | --- | --- | --- | --- | --- |
|  | 5-HT | NA | DA | 5-HT | NA | DA |
| Radioligand | [$^3$H]Paroxetine | [$^3$H]Nisoxetine | [$^3$H]GBR 12935 | [$^3$H]Paroxetine | [$^3$H]Nisoxetine | [$^3$H]GBR 12935 |
| Concentration (nM) | 0.03 | 0.6 | 1 | 0.1 | 2 | 2 |
| NSB defined by | Citalopram | Mazindol | Mazindol | Citalopram | Mazindol | Mazindol |
| Concentration (µM) | 1 | 1 | 1 | 1 | 1 | 1 |
| Species | Rat | Rat | Rat | Human | Human | Human |
| Brain region | Frontal cortex | Frontal cortex | Striatum | Putamen | Thalamus | Putamen |
| Tissue (mg/tube) | 2 | 10 | 1 | 5 | 10 | 4 |
| Incubation (min) | 120 | 240 | 90 | 90 | 240 | 90 |
| Incubation ° C. | 22 | 4 | 4 | 22 | 0 | 4 |
| Drug concentration (M) | $10^{-10}$–$10^{-4}$ | $10^{-9}$–$10^{-3}$ | $10^{-9}$–$10^{-4}$ | $10^{-10}$–$10^{-4}$ | $10^{-9}$–$10^{-4}$ | $10^{-9}$–$10^{-4}$ |

5-HT = 5-hydroxytryptamine,
NA = noradrenaline,
DA = dopamine.
NSB = Non-specific binding.

TABLE 2

Affinity of the (+)- and (−)-enantiomers of sibutramine, and racemic sibutramine for monoamine reuptake sites in rat and human brain

|  | Rat | | | Human | | |
| --- | --- | --- | --- | --- | --- | --- |
| Compound | 5-HT | NA | DA | 5-HT | NA | DA |
| (+)Sibutramine | 2274 ± 263 [0.99 ± 0.03] | 3041 ± 233 [1.02 ± 0.06] | 1652 ± 175 [1.74 ± 0.20] | 369 ± 27 [1.24 ± 0.06] | 2535 ± 452 [0.97 ± 0.13] | 897 ± 125 [1.29 ± 0.04] |

TABLE 2-continued

Affinity of the (+)- and (−)-enantiomers of sibutramine, and racemic sibutramine for monoamine reuptake sites in rat and human brain

| Compound | Rat | | | Human | | |
|---|---|---|---|---|---|---|
| | 5-HT | NA | DA | 5-HT | NA | DA |
| (−)Sibutramine | 944 ± 112 | 23792 ± 615 | 4477 ± 65 | 1226 ± 93 | 11233 ± 2519 | 2890 ± 363 |
| | [1.10 ± 0.03] | [1.02 ± 0.08] | [2.07 ± 0.16] | [1.21 ± 0.09] | [1.30 ± 0.04] | [1.25 ± 0.05] |
| Sibutramine | 2135 ± 137 | 86 ± 10 | 3072 ± 50 | 298 ± 65 | 5451 ± 1160 | 943 ± 64 |
| | [1.262 ± 0.05] | [1.02 ± 0.02] | [1.14 ± 0.04] | [0.85 ± 0.15] | [1.34 ± 0.01] | [1.15 ± 0.04] |

5-HT = 5-hydroxytryptamine,
NA = noradrenaline,
DA = dopamine
Values are inhibition constants ($K_i$s) in nanomolar with Hill slopes in [ ] and are means ± SEM for three or four independent determinations.

5-HT Reuptake Site Binding Assay in Rat Brain
a) Membrane Preparation

Adult male CD rats were killed by cervical dislocation, brains removed and frontal cortices (120–150 mg) immediately dissected.

Tissue was homogenised in ice-cold 0.25 M sucrose (1:30 w/v) using a Kinematic polytron (speed setting 6 for 30 seconds) and centrifuged at 1000 g for 12 minutes. The supernatant was stored on ice and the pellet was resuspended in 0.25 M sucrose (1:20 w/v) and centrifuged at 850 g for 10 minutes. Combined supernatants were diluted 1:100 w/v with ice-cold 50 mM Tris-HCl, pH 7.5 (at 25° C.) containing 120 mM sodium chloride and 5 mM potassium chloride (Tris buffer) and centrifuged at 40,000 g for 10 minutes. The resulting pellet was resuspended in 50 mM Tris buffer (1:100 w/v) and recentrifuged at 40,000 g for 10 minutes. The final pellet was resuspended in 50 mM Tris buffer (equivalent to 2 mg wet weight of tissue/ml) and used immediately in the binding assay. All centrifugations were carried out at 4° C.

b) Binding Assay

Membranes (1000 μl; equivalent to 2 mg wet weight of tissue/tube) were incubated with 200 μl [$^3$H]paroxetine at a single concentration of 30 pM and 200 μl of distilled water (total binding) or 200 μl of test compound at 10 concentrations ranging from $10^{-10}$–$10^{-4}$ M) or 200 μl of citalopram (1 μM; non-specific binding) for 2 h at 22° C.

Membrane bound radioactivity was recovered by filtration under vacuum through Whatman GF/C filters using a Brandel cell harvester. Filters were rapidly washed with 16 ml ice-cold 50 mM Tris buffer and radioactivity determined by liquid scintillation counting (2 ml Packard MV Gold scintillator).

5-HT Reuptake Site Binding Assay in Human Brain
a) Membrane Preparation

Frozen putamen was homogenised in ice-cold 0.25 M sucrose (1:40 w/v) using a motor driven teflon pestle (8 strokes at 120 rpm). The homogenate was centrifuged at 1000 g for 10 min to remove cell debris and myelin. The supernatant was stored on ice and the pellet was rehomogenised in 0.25 M sucrose (1:20 w/v) and centrifuged at 750 g for 10 min to maximise recovery of membranes. The combined supernatants were diluted (1:100 w/v) with 50 mM Tris-HCl, pH 7.5 (at 25° C) containing 120 mM sodium chloride and 5 mM potassium chloride (Tris buffer) and centrifuged at 35,000 g for 10 min. The resulting pellet was resuspended in 50 mM Tris buffer (1:100 w/v) and recentrifuged at 35,000 g for 10 minutes. The final pellet was resuspended in 50 mM Tris buffer (equivalent to 25 mg wet weight of tissue/ml) and used immediately in the binding assay. All centrifugations were carried out at 4° C.

b) Binding Assay

Membranes (200 μl, equivalent to 5 mg wet weight of tissue/tube), 1500 μl 50 mM Tris-HCl, pH 7.5 (at 25° C.) containing 120 mM sodium chloride and 5 mM potassium chloride, 100 μl [$^3$H]paroxetine at a single concentration of 0.1 nM and 100 μl of distilled water (total binding) or 100 μl of test compound (at 10 concentrations ranging from $10^{-10}$–$10^{-5}$ M) or 100 μl of citalopram (1 μM; non-specific binding) were incubated for 90 min at 22° C.

Membrane bound radioactivity was recovered by filtration under vacuum through Whatman GF/C glass fibre filters using a Brandel cell harvester. Filters were rapidly washed with 16 ml ice-cold Tris buffer, and radioactivity determined by liquid scintillation counting.

Noradrenaline Reuptake Site Binding Assay in Rat Brain
a) Membrane Preparation

Adult male CD rats were killed by cervical dislocation, brains removed and frontal cortices (120–150 mg) immediately dissected. Tissue was homogenised in ice-cold 50 mM Tris-HCl, pH 7.4 (at 25° C.) containing 120 mM sodium chloride and 5 mM potassium chloride (Tris buffer; 1:60 w/v) using a Kinematic polytron (speed setting 6 for 30 seconds) and centrifuged at 40,000 g for 10 minutes. The supernatant was discarded and the pellet rehomogenised in Tris buffer, 1:60 w/v, and centrifuged at 40,000 g for 10 minutes. This step was repeated a further twice so that, in total, the brain tissue was homogenised and centrifuged four times. The final pellet was resuspended in 50 mM Tris-HCl, pH 7.4 containing 300 mM sodium chloride and 5 mM potassium chloride (equivalent to 25 mg wet weight of tissue/ml) and used immediately in the binding assay. All centrifugations were carried out at 4° C.

b) Binding Assay

Membranes (400 μl; equivalent to 10 mg wet weight of tissue/tube) were incubated with 50 μl [$^3$H]nisoxetine at a single concentration of 0.6 nM and 50 μl of distilled water (total binding) or 50 μl of test compound (at 10 concentrations ranging from $10^{-9}$–$10^{-3}$ M) or 50 μl of mazindol (1 μM; non-specific binding) for 4 h at 4° C.

Membrane bound radioactivity was recovered by filtration under vacuum through Skatron 11734 filters using a Skatron cell harvester. Filters were rapidly washed with ice-cold 50 mM Tris-HCl, pH 7.4 containing 120 mM sodium chloride and 5 mM potassium chloride (wash setting 9,9,0) and radioactivity determined by liquid scintillation counting (1 ml Packard MV Gold scintillator).

Noradrenaline Reuptake Site Binding Assay in Human Brain
a) Membrane Preparation Frozen thalamus was homogenised in ice-cold 0.25 M sucrose (1:40 w/v) using a motor driven teflon pestle (8 strokes at 120 rpm). The homogenate was centrifuged at 1000 g for 10 min to remove cell debris and myelin. The supernatant was stored on ice and the pellet was rehomogenised in 0.25 M sucrose (1:20 w/v) and centrifuged at 750 g for 10 min to maximise recovery of membranes. The combined supernatants were diluted (1:100 w/v) with 50 mM Tris-HCl, pH 7.4 (at 25° C.) containing 300 mM sodium chloride and 5 mM potassium chloride (Tris buffer) and centrifuged at 35,000 g for 10 min. The pellet was resuspended in Tris buffer (1:40 w/v) and incubated at 37° C. for 10 min (to remove endogenous neurotransmitters) and recentrifuged at 35,000 g for 10 minutes. The final pellet was resuspended in 50 mM Tris buffer (equivalent to 28.6 mg wet weight of tissue/ml) and used immediately in the binding assay. All centrifugations were carried out at 4° C.
b) Binding Assay Membranes (350 µl, equivalent to 10 mg wet weight of tissue/tube), 50 µl of 50 mM Tris-HCl, pH 7.4 (at 25° C.) containing 300 mM sodium chloride and 5 mM potassium chloride, 50 µl of [$^3$H]nisoxetine at a single concentration of 2 nM and 50 µl of distilled water (total binding) or 100 µl of test compound (at 10 concentrations ranging from $10^{-9}$–$10^{-4}$ M) or 100 µl of mazindol (1 µM; non-specific binding) were incubated for 4 h at 0° C.

Membrane bound radioactivity was recovered by filtration under vacuum through Whatman GF/C glass fibre filters using a Brandel cell harvester. Filters were rapidly washed with 16 ml ice-cold Tris buffer, and radioactivity determined by liquid scintillation counting.

Dopamine Reuptake Site Binding Assay in Rat Brain
a) Membrane Preparation

Adult male CD rats were killed by cervical dislocation, brains removed and striata (50–80 mg) immediately dissected. Tissue was homogenised in ice-cold 0.32 M sucrose (1:80 w/v) using a motor driven teflon pestle (12 strokes, 800 rpm) and centrifuged at 1000 g for 12 minutes. The supernatant was stored on ice and the pellet was resuspended in 0.32 M sucrose (1:80 w/v) and centrifuged at 850 g for 10 minutes. Combined supernatants were diluted to 1:320 w/v with ice-cold 50 mM Tris-HCl, pH 7.4 (at 25° C.) containing 200 mM sodium chloride and 5 mM potassium chloride and centrifuged at 40,000 g for 10 minutes. The resulting pellet was resuspended in 10 ml of 50 mM Tris buffer, incubated at 37° C. for 10 min, diluted in 50 mM Tris buffer (1:320 w/v) and recentrifuged at 40,000 g for 10 minutes. The final pellet was resuspended in 50 mM Tris buffer (equivalent to 1.25 mg wet weight of tissue/ml) and used immediately in the binding assay. All centrifugations were carried out at 4° C.

b) Binding Assay

Membranes (800 µl; equivalent to 1 mg wet weight of tissue/tube) were incubated with 100 µl [$^3$H]GBR 12935 at a single concentration of 1 nM and 100 µl of distilled water (total binding) or 100 µl of test compound (at 10 concentrations ranging from $10^{-9}$–$10^{-4}$ M) or 100 µl of mazindol (1 µM; non-specific binding) for 90 min at 4° C.

Membrane bound radioactivity was recovered by filtration under vacuum through Whatman GF/C filters, presoaked for 1 h in 0.5% polyethylenimine, using a Brandel cell harvester. Filters were rapidly washed with 16 ml of ice-cold 50 mM Tris-HCl, pH 7.4 and radioactivity determined by liquid scintillation counting (2 ml Packard MV Gold scintillator).

Dopamine Reuptake Site Binding Assay in Human Brain
a) Membrane Preparation

Frozen putamen was homogenised in ice-cold 0.25 M sucrose (1:40 w/v) using a motor driven teflon pestle (8 strokes at 120 rpm). The homogenate was centrifuged at 1000 g for 10 min to remove cell debris and myelin. The supernatant was stored on ice and the pellet was rehomogenised in 0.25 M sucrose (1:20 w/v) and centrifuged at 750 g for 10 min to maximise recovery of membranes. The combined supernatants were diluted (1:100 w/v) with 50 mM Tris-HCl, pH 7.4 (at 25° C.) containing 200 mM sodium chloride and 5 mM potassium chloride (Tris buffer) and centrifuged at 35,000 g for 10 min. The membrane pellet was resuspended in Tris buffer (1:40 w/v) and incubated at 37° C. for 10 min (to remove endogenous neurotransmitters) and recentrifuged at 35,000 g for 10 minutes. The final pellet was resuspended in 50 mM Tris buffer (equivalent to 5 mg wet weight of tissue/ml) and used immediately in the binding assay. All centrifugations were carried out at 4° C.
b) Binding Assay Membranes (800 µl, equivalent to 4 mg wet weight of tissue/tube), 100 µl of [$^3$H]GBR 12935 at a single concentration of 2 nM and 100 µl of distilled water (total binding) or 100 µl of test compound (at 10 concentrations ranging from $10^{-9}$–$10^{-4}$ M) or 100 µl of mazindol (1 µM; non-specific binding) were mixed thoroughly and incubated for 90 min at 0° C.

Membrane bound radioactivity was recovered by filtration under vacuum through Whatman GF/C glass fibre filters, pre-soaked for 1 h in 0.5% polyethylenimine, using a Brandel cell harvester. Filters were rapidly washed with 16 ml ice-cold Tris buffer, and radioactivity determined by liquid scintillation counting.

In Vivo Tests
1) Anti-depressant Screens
a) Porsolt Test in Mice

This test was carried out according to the procedure described in Porsolt, R. D. (1981). Behavioural despair. In: Antidepressants: Neurochemical, Behavioural and Clinical Perspectives, ed. S. J. Enna et al, pp. 121–139. New York: Raven Press.
b) Reserpine Reversal Screen This was carried as described in U.S. Pat. No. 4,746,680 except that the dose of reserpine was 10 mg/kg (i.p.).

The test compounds were dissolved in deionised water. Control groups of mice were treated with either deionised water or the standard antidepressant, amitriptyline (30 mg/kg p.o.).
Prevention of Reserpine-induced Ptosis in Rats A further standard test for antidepressants but relying on the ability of compounds to prevent rather than reverse reserpine-induced effects in rodents.

The compounds were tested as described in Prog. Neuro-Psychopharmacol. & Biol. Psychiat., 12, 575–584, Buckett et al. Rats were housed five per cage rather than six per cage and ptosis was assessed twice during 60 sec rather than during 30 sec.
Analysis of Data Data from the reserpine reversal screen in mice and the reserpine prevention test in rats were used to calculate $ED_{50}$ values for the reversal and prevention of reserpine-induced effects respectively.

Data from the Porsolt test were analysed in two ways. Data from the two experiments where all doses of each compound were tested concurrently were combined and an $ED_{50}$ value (dose required to increase mobility by 50%) was calculated by linear regression after log transformation of the doses. These data were combined with those obtained from an additional test to derive the $LED_{50}$, the lowest effective dose to induce a 50% increase in the mobility of mice compared to concurrently treated control mice, which is the standard measure of activity in this model.

Results

TABLE 3

| Compound | Porsolt test in mice | Reserpine test in mice | Reserpine test in rats |
|---|---|---|---|
| (+/−)-Sibutramine | 1.8 | 1.8 | ~1.5 |
| (+)-Sibutramine | 2.4 | ~1.0 | 0.7 |
| (−)-Sibutramine | 9.8 | ~30.0 | 59 |

Data given as $ED_{50}$ (mg/kg)

Food Intake Studies

Materials and Methods

The effects of sibutramine and its enantiomers on the food intake of laboratory rats were determined by measuring the amounts of food ingested over the 24 hour period following acute administration.

Animals

The study was carried out on a homogeneous group of 12 adult male, Sprague-Dawley rats (Ico. OFA-SD IOPS caw) supplied by Iffa-Creda (L'Arbresle, France). They were of the same age and had been reared under identical conditions with an identical diet since birth. Only male rats were employed to avoid interference between the ovarian cycle and feeding behaviour. The animals had not been subjected to any previous experimentation. They weighed 200 g (1 week prior to arrival in the laboratory) and were six weeks old. At the start of experimentation they had a mean weight of 433.2 g (range 412–477 g; SEM 5.5 g).

Rearing Conditions

The rats were housed individually in large cubic cages (40 cm per side), specially designed for studies on food intake. All spilled food was recovered, and each cage was equipped with individual lighting and a nest box to favour regular feeding behaviour.

The cages were placed in a recognised animal house conforming to good laboratory practice. Room temperature, sound level, humidity and light cycle were strictly controlled. The main environmental parameters (temperature, 24±2° C. and relative humidity, 45%) were recorded continuously.

Light Cycle

Since the rat is essentially a nocturnal animal, it consumes most (60–80%) of its calorie intake in the dark phase of the circadian cycle. To enable measurements to be made in normal working hours, the animals were habituated to a reversed light cycle with eight hours darkness and 16 hours light, with the onset of the dark phase at 09.00 h. This enabled evaluation of the time course of the effect of compounds over the whole dark phase. The rats were habituated to the reversed light cycle, handling and gastric intubation for a period of five weeks.

Diet

The rats had ad libitum access to tap water and normal laboratory chow (Extralabo M20, Piétrement, 77650 Longeville, France) in the form of round bars (15 mm diam, 10–25 mm long).

Compounds

Posing

The activities of sibutramine and its (+)- and (−)-enantiomers were evaluated using the same group of 12 rats in two series of experiments. Over the various experimental sessions, each group received the following treatments accoding to a randomisation schedule.

| Series 1 | | Series 2 | |
|---|---|---|---|
| racemic sibutramine: | 10 mg/kg po | (−)-enantiomer: | 1.0 mg/kg po |
| racemic sibutramine: | 3.0 mg/kg po | (−)-enantiomer: | 10 mg/kg po |
| (+)-enantiomer: | 1.0 mg/kg po | (−)-enantiomer: | 30 mg/kg po |
| (+)-enantiomer: | 3.0 mg/kg po | placebo: | vehicle (ultra-pure water) po |
| (−)-enantiomer: | 1.0 mg/kg po | | |
| (−)-enantiomer: | 3.0 mg/kg po | | |
| placebo: | vehicle (ultra-pure water) po | | |

Each rat received all of the various doses of test compound and placebo. Each dose was tested in every experimental session.

Dosing

Compounds were dissolved in ultrapure water immediately after dosing. All the doses were administered in a volume of 2 ml/kg. An identical volume of vehicle (ultrapure water) was administered as placebo.

Route and Time of Administration

The compounds were administered via an intragastric tube (Carrieri, France). Compounds were given between 08.00 h and 08.30 h and the animals were allowed access to their usual diet, immediately before the start of the dark phase at 09.00 h.

Spacing of Experimental Sessions

A gap of three days was left between sessions for the first series and one week for the second series. This was believed to be long enough for adequate wash-out. However, prior to each experimental session, a possible residual effect was evaluated by comparing mean food intake between treatment groups during the 24 hours before the next experimental session.

Between consecutive experimental sessions, the rats had ad libitum access to food and water and were left undisturbed apart from the weighing of food described above.

Measurements

Principal Measurement

Cumulative food intake was measured after acute administration of the test compounds. The measurements were made every hour over the eight-hour dark phase of the circadian cycle. A final measurement was made 24 hours after administration, at the end of the following diurnal cycle.

Control Measurements

These consisted of an identical set of measurements of food intake after administration of placebo under the same conditions as those used for the test compounds.

Timing and Number of Measurements of Food Inntake

The measurements of food intake were carried out during the nocturnal, hyperphagic phase in animals with previous ad libitum access to food. Animals were temporarily deprived of food for around 60 min at the end of the light phase (08.00 h to 09.00 h) before each experimental session to enable the cages to be cleaned.

The amount of food ingested by each animal was determined by weighing the food pots after careful recovery of spillage. The measurements were made after access to the food for 30 and 60 min and then each hour until the end of the dark phase at 17.00 h. A final measurement was made on the following day, 24 hours after administration of test compound or placebo. Overall, 10 measurements were made for each rat in each experimental session.

Expression of Results and Statistical Analysis

The results were expressed as mean food intake at various times after each administration of test compound or placebo.

The means were compared by analysis of variance (ANOVA) for one repeated factor (animal number) and two fixed factors (A. treatment or dose, and B. time of measurement). Individual means were compared post-hoc using the Newman-Keul's test, and results were considered significant if p<0.05.

The 50% effective dose ($ED_{50}$) was that of sibutramine or its enantiomers which over a given period induced a 50% reduction in food intake from the start of the experiment with respect to the food intake of animals receiving placebo.

Results

The base line readings demonstrated that there were no residual effects of the compounds at the end of the washout period.

Food Intake After Administration of Test Compounds

50% Effective Dose ($ED_{50}$)

According to the procedure used in this study (food intake measured during dark phase following intragastric administration, 30 to 60 min before access to food at the start of the dark phase) the $ED_{50}$ values for the different compounds at the end of the dark phase were estimated to be:

(+)-enantiomer: ~1 mg/kg (−)-enantiomer: >10 mg/kg sibutramine: ~2 mg/kg

What is claimed is:

1. A method of treating depression in a human which comprises administering to a human in need of antidepressant therapy, an amount of (+)-sibutramine, or a pharmaceutically acceptable salt thereof, substantially free of its (−)-stereoisomer, said amount being sufficient to alleviate depression.

2. A method of treating depression in a human according to claim 1 in which said amount of (+)-sibutramine or a pharmaceutically acceptable salt thereof, substantially free of its (−)-stereoisomer, is sufficient to alleviate depression but insufficient to cause adverse effects associated with the administration of racemic sibutramine.

3. The method of claims 1 or 2 wherein (+)-sibutramine is administered by intravenous infusion, transdermal delivery, or orally as a tablet or a capsule.

4. The method of claim 3 wherein the amount administered is from about 1 mg to about 60 mg per day.

5. The method of claim 4 wherein the amount administered is from about 2 mg to about 50 mg per day.

6. The method of claim 5 wherein the amount administered is from about 5 mg to about 45 mg per day.

7. The method of claim 3 wherein the amount of (+)-sibutramine or a pharmaceutically acceptable salt thereof is greater than approximately 90% by weight of the total amount of sibutramine.

8. The method of claim 3 wherein the (+)-sibutramine or a pharmaceutically acceptable salt thereof, substantially free of its (−)-stereoisomer, is administered together with a pharmaceutically acceptable carrier.

9. The method according to claim 3 wherein (+)-sibutramine is administered as a hydrochloride salt.

10. A method for treating obesity or weight gain in a human which comprises administering to a human in need of a reduction in weight, an amount of (+)-sibutramine or a pharmaceutically acceptable salt thereof, substantially fie of its (−)stereoisomer, said amount being sufficient to alleviate obesity or weight gain.

11. A method for treating obesity or weight gain in a human according to claim 10 wherein said amount is sufficient to alleviate obesity or weight gain but insufficient to cause adverse effects associated with administration of racemic sibutramine.

12. The method of claims 10 or 11 wherein (+)-sibutramine is administered by intravenous infusion, transdermal delivery, or orally as a tablet or a capsule.

13. The method of claim 12 wherein the amount administered is from about 1 mg to about 60 mg per day.

14. The method of claim 13 wherein the amount administered is from about 2 mg to about 50 mg per day.

15. The method of claim 14 wherein the amount administered is from about 5 mg to about 45 mg per day.

16. The method of claim 15 wherein the amount of (+)-sibutramine or a pharmaceutically acceptable salt thereof is greater than approximately 90% by weight of the total amount of sibutramine.

17. The method of claim 12 wherein the (+)-sibutramine or a pharmaceutically acceptable salt thereof, substantially free of its (−)-stereoisomer, is administered together with a pharmaceutically acceptable carrier.

18. The method according to claims 10 or 11 wherein (+)-sibutramine is administered as a hydrochloride salt.

19. A method of treating disorders ameliorated by inhibition of neuronal monoamine reuptake in a human which comprises administering to a human in need of such treatment an amount of (+)-sibutramine or a pharmaceutically acceptable salt thereof, substantially free of its (−)-stereoisomer, said amount being sufficient to alleviate said disorders.

20. A method of treating disorders ameliorated by inhibition of neuronal monoamine reuptake in a human according to claim 19 in which said amount is sufficcient to alleviate said disorders but insufficient to cause adverse effects associated with administration of racemic sibutramine.

21. A method of treating disorders ameliorated by inhibition of neuronal monoamine reuptake in a human according to claims 19 or 20 wherein said monoamine is dopamine.

22. A method of treating disorders ameliorated by inhibition of neuronal monoamine reuptake in a human according to claims 19 or 20 wherein said disorder is Parkinson's disease.

23. The method of claims 19 or 20 wherein (+)-sibutramine is administered by intravenous infusion, transdermal delivery, or orally as a tablet or a capsule.

24. The method of claim 23 wherein the amount administered is from about 1 mg to about 60 mg per day.

25. The method of claim 24 wherein the amount administered is from about 2 mg to about 50 mg per day.

26. The method of claim 25 wherein the amount administered is from about 5 mg to about 45 mg per day.

27. The method of claim 23 wherein the amount of (+)-sibutramine or a pharmaceutically acceptable salt thereof is greater than approximately 90% by weight of the total amount of sibutramine.

28. The method of claim 23 wherein (+)-sibutramine or a pharmaceutically acceptable salt thereof, substantially free of its (−)-stereoisomer is administered together with a pharmaceutically acceptable carrier.

29. The method according to claim 23 wherein (+)-sibutramine is administered as a hydrochloride salt.

* * * * *